(12) United States Patent
Lai et al.

(10) Patent No.: US 9,207,200 B2
(45) Date of Patent: Dec. 8, 2015

(54) BIOSENSOR STRIP

(71) Applicant: OK BIOTECH CO. LTD., Hsinchu (TW)

(72) Inventors: Chia-Te Lai, Hsinchu (TW); An-Yuan Lee, Hsinchu (TW)

(73) Assignee: OK BIOTECH CO. LTD., Hsinchu (TW)

( * ) Notice: Subject to any disclaimer, the term of this patent is extended or adjusted under 35 U.S.C. 154(b) by 238 days.

(21) Appl. No.: 13/935,845

(22) Filed: Jul. 5, 2013

(65) Prior Publication Data
US 2014/0008219 A1    Jan. 9, 2014

(30) Foreign Application Priority Data

Jul. 6, 2012   (TW) .............................. 101213099 U

(51) Int. Cl.
*G01N 27/327* (2006.01)

(52) U.S. Cl.
CPC .......... *G01N 27/327* (2013.01); *G01N 27/3272* (2013.01)

(58) Field of Classification Search
CPC .............. C12Q 1/00; C12Q 1/02; C12Q 1/34; C12Q 1/54; G01N 27/327; G01N 27/3272; A61B 5/150274; C23C 28/00
See application file for complete search history.

(56) References Cited

U.S. PATENT DOCUMENTS

| | | | | |
|---|---|---|---|---|
| 6,241,862 | B1 * | 6/2001 | McAleer et al. | 204/403.05 |
| 2004/0194302 | A1 * | 10/2004 | Bhullar et al. | 29/847 |
| 2011/0132778 | A1 * | 6/2011 | Austera et al. | 205/792 |
| 2011/0139635 | A1 * | 6/2011 | Huang et al. | 205/792 |
| 2012/0043204 | A1 * | 2/2012 | Young et al. | 204/403.14 |
| 2012/0102722 | A1 * | 5/2012 | Wang et al. | 29/592.1 |
| 2013/0084591 | A1 * | 4/2013 | McColl et al. | 435/29 |

* cited by examiner

*Primary Examiner* — Jennifer Dieterle
(74) *Attorney, Agent, or Firm* — WPAT, PC; Justin King

(57) ABSTRACT

A biosensor strip with improved sample area design is disclosed, in which a specimen flowing in a flow channel is siphoned into another flow channel which has two hydrophilic layers attached to two respective sides of the same for enhancing the siphoning of the specimen. In an embodiment, by the doping of a hydrophilic material into an enzyme layer of the biosensor strip, the specimen that is being siphoning rapidly is able to mixed with the enzyme fully so as to enhance the measurement accuracy of a biological instrument using the biosensor strip.

7 Claims, 1 Drawing Sheet

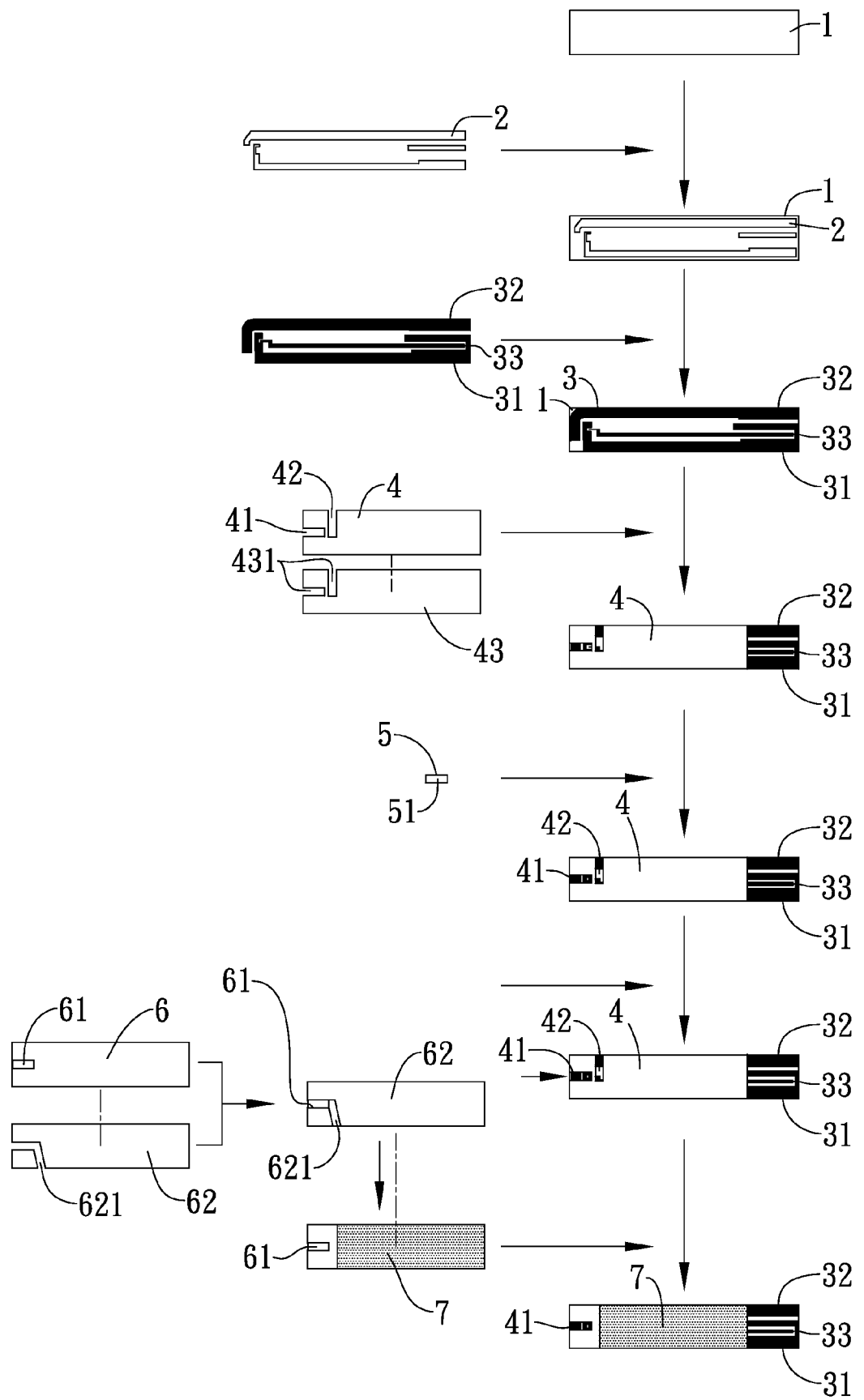

BIOSENSOR STRIP

FIELD OF THE INVENTION

The present invention relates to a biosensor strip, and more particularly, to a biosensor strip with improved sample area design for enabling a specimen that is flowing in one flow channel to be siphoned into another flow channel.

BACKGROUND OF THE INVENTION

Nowadays, chronic diseases, such as diabetes, are becoming more and more common in our modern society. Since such chronic diseases are long-term conditions, the treatment generally involves a long-term monitoring of the patient's physical attributes and also certain on-site emergency examinations. However, if the monitoring or the examinations are performed in a traditional medical therapy unit, the patient's specimen will be cultured, process so as to react with specific enzymes in laboratory tests that it generally will take a conceivable long period of time just to obtain the test results, and thus can be a torment mentally and physically for patients. Nevertheless, following the advance of biomedical technology, more and more self-inspection apparatuses are becoming available for chronic disease patients to perform the required monitoring and examinations by themselves at home, and then provide the results of such monitoring and examinations lately to their doctors for allowing the doctors to analyze the test results and thus treat the diseases properly.

Conventionally, a biosensor is devised for the detection of an analyte that can be blood, urine or the like collected and sampled from a patient. In the biosensor, the sampled analyte is mixed with a specific enzyme capable of reacting to the analyte, and then this reaction is measured by a biotranducer which outputs a measurable signal proportional to the presence of the target analyte in the sample to a medical test equipment to produce a report. However, in those conventional bipsensor strip, the sample area is not designed specifically for assisting the sampled analyte to flow rapidly into the biosensor strip, and thus, insufficient specimen is common which can serverely damage the accuracy of measurement. Therefore, it is in need of a biosensor strip with improved sample area design capable of correcting the abovementioned shortcoming.

SUMMARY OF THE INVENTION

The primary object of the present invention is to provide a biosensor strip with improved sample area design, in which a specimen flowing in a flow channel is siphoned into another flow channel which has two hydrophilic layers attached to two respective sides of the same for enhancing the siphoning of the specimen. In an embodiment, by the doping of a hydrophilic material into an enzyme layer of the biosensor strip, the specimen that is being siphoning rapidly is able to mixed with the enzyme fully so as to enhance the measurement accuracy of a biological instrument using the biosensor strip.

To achieve the above object, the present invention provides a biosensor strip, for collecting and receiving a specimen while electrically connected to a biological instrument for allowing the biological instrument to generate a value of measurement, the biosensor comprising:
 a substrate;
 a carbon layer, disposed on a surface of the substrate, further comprising three conducting wires that are electrically connected to the biological instrument;
 a first hydrophilic layer, disposed on a surface of the carbon layer through the spacing of a first insulated layer, having a reaction zone and a first hydrophilic guiding area formed thereon;
 an enzyme layer, disposed on the reaction zone of the first hydrophilic layer, having a hydrophilic material doped therein;
 a second hydrophilic layer, disposed on a surface of the first hydrophilic layer through the spacing of a second insulated layer, having a reaction gap and a second hydrophilic guiding area formed thereon at positions corresponding respectively to the reaction zone and the first hydrophilic guiding area of the first hydrophilic layer; and
 a surface layer, disposed on a surface of the second hydrophilic layer.

In an exemplary embodiment, the biosensor strip further comprises: a silver layer, disposed sandwiching between the substrate and the carbon layer.

In an exemplary embodiment, the silver layer is attached to a surface of the substrate by a printing means.

In an exemplary embodiment, the carbon layer is attached to a surface of the substrate or a surface of the silver layer by a printing means.

In an exemplary embodiment, there can be a pattern or a letter printed on a surface of the surface layer.

In an exemplary embodiment, at least one conducting wire of the three conducting wires of the carbon layer is used for measuring the proportion of the presence of a target specimen in a sample.

In an exemplary embodiment, the first insulated layer is formed with a gap at a position corresponding to the reaction zone and the first hydrophilic guiding area.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein:
 FIG. 1 is an exploded view of a biosensor strip according to an embodiment of the present invention.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Please refer to FIG. 1, which is an exploded view of a biosensor strip according to an embodiment of the present invention. As shown in FIG. 1, after collecting a specimen, the biosensor strip is electrically connected to a biological instrument, such as a glucose meter, so as to allow the biological instrument to generate a value of measurement, and the biosensor strip comprises: a substrate 1; a silver layer 2; a carbon layer 3, disposed on a surface of the substrate 1, further comprising three conducting wires, i.e. a first conducting wire 31, a second conducting wire 32 and a third conducting wire 33 in this embodiment, that are electrically connected to the biological instrument while enabling at least one conducting wire of the three conducting wires of the carbon layer, i.e. the third conducting wire 33, to be used for measuring the proportion of the presence of a target specimen in a sample and consequently showing a signal for insufficient specimen on the biological instrument when the is not enough specimen for testing; a first hydrophilic layer 4, disposed on a surface of the carbon layer 3 through the spacing of a first insulated layer 43, having a reaction zone 41 and a first hydrophilic guiding area 42 formed thereon while enabling the first insulated layer 43 to be formed with gaps 431 at positions corresponding to the reaction zone 41 and the first hydrophilic guiding area 42; an enzyme layer 5, disposed on the reaction zone 41 of the first hydrophilic layer 4, having a hydrophilic material 51 doped therein that the hydrophilic material 51 is provided for enabling the specimen to attach to the enzyme layer 5 more easily and thus mixed into the enzyme layer 5 fully without interfering the measurement result of the biological instrument; a second hydrophilic layer 6, disposed on a surface of the first hydrophilic layer 4 through the spacing of a second insulated layer 62, having a reaction gap 61 and a second hydrophilic guiding area 621 formed thereon at positions corresponding respectively to the reaction zone 41 and the first hydrophilic guiding area 42 of the first hydrophilic layer 4; and a surface layer 7, disposed on a surface of the second hydrophilic layer 6, having a pattern or letter printed thereon whereas the pattern or the letter is the trademark of a bio sensor manufacturer.

Operationally, when a specimen, such as a sample of blood or urine, is being brought near the reaction zone 41 of the biosensor strip of FIG. 1, the specimen can be drawn to flow rapidly from the reaction zone 41 and the gap 61 to the first and the second hydrophilic guiding areas 42 and 621 while being distribute evenly therein. After the specimen in the reaction zone 41 encounters the enzyme layer 5, an electrochemical reaction is enabled so as to produce an electric potential accordingly. Thereafter, the electrical potential can be detected by the first, the second and the third conducting wires 31, 32, 33 and consequently a measurable signal is outputted from the three conducting wires 31, 32, 33 to the biological instrument to produce a report. To sum up, the present invention provides a biosensor strip with improved sample area design, in which a specimen flowing in a flow channel is siphoned into another flow channel which has two hydrophilic layers attached to two respective sides of the same for enhancing the siphoning of the specimen. In an embodiment, by the doping of a hydrophilic material into an enzyme layer of the biosensor strip, the specimen that is being siphoning rapidly is able to mixed with the enzyme fully so as to enhance the measurement accuracy of a biological instrument using the bio sensor strip.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A biosensor strip, for collecting and receiving a specimen while electrically connected to a biological instrument for allowing the biological instrument to generate a value of measurement, the biosensor strip comprising:
   a substrate;
   a carbon layer, disposed on a surface of the substrate, further comprising three conducting wires that are electrically connected to the biological instrument;
   a first insulated layer, disposed on said carbon layer;
   a first hydrophilic layer, disposed on said first insulated layer, comprising:
      a reaction zone; and
      a first hydrophilic guiding area, disposed internally within the biosensor strip with respect to said reaction zone;
   an enzyme layer, disposed on the reaction zone of the first hydrophilic layer, having a hydrophilic material doped therein;
   a second insulated layer, disposed on said first hydrophilic layer;
   a second hydrophilic layer, disposed on said second insulated layer, comprising:
      a reaction gap; and
      a second hydrophilic guiding area, disposed internally within the biosensor strip with respect to said reaction gap, corresponding to the reaction zone and the first hydrophilic guiding area; and
   a surface layer, disposed on a surface of the second hydrophilic layer,
   wherein upon said specimen flowing into said reaction zone, said specimen is further siphoned into said first hydrophilic guiding area and said second hydrophilic guiding area.

2. The biosensor strip of claim 1, further comprising:
   a silver layer, disposed between the substrate and the carbon layer.

3. The biosensor strip of claim 2, wherein the silver layer is attached to a surface of the substrate by a printing means.

4. The biosensor strip of claim 3, wherein the carbon layer is attached to a surface of the substrate or a surface of the silver layer by a printing means.

5. The biosensor strip of claim 1, wherein there is a pattern or a letter printed on a surface of the surface layer.

6. The biosensor strip of claim 1, wherein at least one conducting wire of the three conducting wires of the carbon layer is used for detecting an insufficiency of said specimen for said generation of said value.

7. The biosensor strip of claim 1, wherein the first insulated layer is further formed with a gap at a position corresponding to the reaction zone and the first hydrophilic guiding area.

* * * * *